United States Patent [19]

Kobayashi

[11] Patent Number: 5,026,887

[45] Date of Patent: Jun. 25, 1991

[54] METAL-CONTAINING POLYMER AND PRODUCTION PROCESS THEREOF

[76] Inventor: Shiro Kobayashi, 1-1-302, Kawauchi Juutaku, Kawauchi Mubanchi, Sendai-shi, Miyagi, 980, Japan

[21] Appl. No.: 498,501

[22] Filed: Mar. 26, 1990

[30] Foreign Application Priority Data

Apr. 20, 1989 [JP] Japan .................... 1-98695

[51] Int. Cl.$^5$ .......................... C07F 7/22; C07F 7/24; C07F 7/02; C07F 7/30
[52] U.S. Cl. ............................... 556/81; 556/9; 556/12; 556/87; 556/410; 556/413
[58] Field of Search ................. 556/9, 12, 81, 87, 410, 556/413

[56] References Cited

U.S. PATENT DOCUMENTS

| | | | |
|---|---|---|---|
| 4,058,400 | 11/1977 | Crivello | 556/81 X |
| 4,119,614 | 10/1978 | King et al. | 556/81 X |
| 4,260,552 | 4/1981 | Strunk et al. | 556/9 X |
| 4,654,368 | 3/1987 | Sakamoto et al. | 556/9 X |

*Primary Examiner*—Arthur C. Prescott
*Attorney, Agent, or Firm*—Armstrong, Nikaido, Marmelstein, Kubovcik & Murray

[57] ABSTRACT

A metal-containing polymer represented by the general formula:

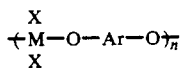

where M represents a group IV metal atom, X represents $N(SiR^1R^2R^3)_2$ or $N(R^4)SiR^1R^2R^3$, each of $R^1$, $R^2$, $R^3$ and $R^4$ represents an alkyl group or aryl group, Ar represents a (substituted) phenylene, (substituted) naphthylene or (substituted) anthrylene group, and n represents an integer of 2 to 5000.

The polymer can be produced by the oxidation-reduction alternating copolymerization using a reductant monomer represented by $MX_2$ as and substituted-benzoquinones, -naphthoquinones or -anthraquinones as the oxidant monomer.

The polymer is solvent-soluble and can be used as functional materials such as resist materials, electronic materials, etc.

8 Claims, No Drawings ns an integer of 2 to 5000.

METAL-CONTAINING POLYMER AND PRODUCTION PROCESS THEREOF

BACKGROUND OF THE INVENTION

1. Field of the Invention

The present invention concerns a novel polymer that can be used as resist material (for UV, electron rays, etc.), electronics materials (semiconductors, etc.), adhesives and functionally gradient materials.

2. Description of the Prior Art

It has been attempted for synthesizing polymers having group IV metal atoms in the main chain. For instance, a method of conducting redox reaction using $Sn(CH(SiMe_3)_2)_2$ and a substituted p-benzoquinone (refer to Preprint I for The 57th Autumn Meeting of Japan Chemical Society, 1988, p 108, Polymer Preprints, Japan 37(2), 338 (1988)) or a method of reacting $SnCl_2$ and a substituted benzoquinone has been known. However, polymers obtained by such a method are insoluble in solvent and can not be used as the polymer materials, as well as detailed structures for the reaction products are unknown.

It has been considered so far that a soluble polymer with a well-defined structure containing group IV metal atoms in the main chain can not be synthesized because the resultant polymer itself is insoluble or the resultant polymer is highly reactive and becomes insoluble by gelation due to side reactions.

It is, accordingly, an object of the present invention to provide a solvent-soluble polymer, taking notice on the fact that a polymer containing group IV metal atoms in the main chain has a possibility to various application uses such as resist materials, electronics materials or adhesives.

The present inventor has made various studies on the reason why the polymer proposed so far containing the group IV metal atoms in the main chain is insoluble and, as a result, has found that a polymer having high molecular weight and solvent solubility can be obtained by modifying ligands bonding to the group IV metal atoms.

SUMMARY OF THE INVENTION

The foregoing object of the present invention can be attained by a metal-containing polymer containing group IV metal atoms in the main chain represented by the general formula:

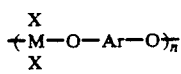

where M represents a group IV metal atom, X represents $N(SiR^1R^2R^3)_2$ or $N(R^4)SiR^1R^2R^3$, each of $R^1$, $R^2$, $R^3$ and $R^4$ represents an alkyl group or aryl group, Ar represents a (substituted) phenylene, (substituted) naphthylene or (substituted) anthrylene group, and n represents an integer of 2 to 5000.

The metal-containing polymer as described above can be produced by conducting alternating oxidation-reduction copolymerization using a compound represented by the general formula:

$$MX_2$$

where M represents a group IV metal atom, X represents $N(SiR^1R^2R^3)_2$ or $N(R^4)SiR^1R^2R^3$, each of $R^1$, $R^2$, $R^3$ and $R^4$ represents an alkyl group or aryl group, as a reductant monomer, and (substituted) benzoquinones, (substituted) naphthoquinones or (substituted) anthraquinones as an oxidant monomer.

In the present invention, the group IV metal atom can include, silicon, germanium, tin and lead, and $R^1$, $R^2$ and $R^3$ bonded to the silicon atom and $R^4$ bonded to the nitrogen atom can include $C_1$–$C_{20}$ alkyl group or aryl group.

As the (substituted) benzoquinones, (substituted) naphthoquinones and (substituted) anthraquinones used as the oxidant monomer, there can be mentioned benzoquinone, naphthoquinone, anthraquinone, as well as alkyl-, aryl-, halogen-, nitrile- substitutes for each of them.

In the present invention, the reaction between a reductant monomer and an oxidant monomer can be conducted by mixing the oxidant monomer and the reductant monomer with or without using an initiator or a catalyst. As the solvent, aromatic solvent such as toluene and benzene or ether solvent such as tetrahydrofuran can be used. The reaction temperature is usually from $-100°$ C. to $100°$ C., preferably, from $-78°$ C. to $50°$ C.

The novel metal-containing polymer according to the present invention is an alternating copolymer of high polymerization degree in which metal atoms and aromatic rings are connected alternatingly by way of oxygen atoms. Although the polymer is a high molecular weight material having a degree of polymerization of greater than 300, it is solvent-soluble and can be formed into a transparent sheet by means of a film casting method and it is expected to be usable as resist material sensitive to UV-rays, electron rays, etc. electronics materials such as semiconductors, adhesives, functionally gradient materials, etc.

EXAMPLE 1

A 2 ml toluene solution containing 1.160 g (2.64 mmol) of bis(bis(trimethylsilyl)amide)tin(II) (hereinafter simply referred to as monomer A) was cooled to $-42°$ C., to which a 5 ml toluene solution containing 0.271 g (2.51 mmol) of p-benzoquinone was dropped, stirred at $-42°$ C. for 30 min, further stirred at a room temperature for 18 hours, concentrated in vacuum and dried. The yield was quantitative.

$^1$H-NMR (CDCl$_3$): $\delta$0.25(s,SiMe$_3$,36H), 6.83(br,Ar,4H).

$^{13}$C-NMR (CDCl$_3$): $\delta$5.31(SiMe$_3$), 120.45(=CH—), 152.11(O—C).

IR (KBr) cm$^{-1}$: 2945,1501,1251,1089,973,899,856,834,751, 672,518.

The weight average molecular weight measured by GPC (Hitachi 655A) was more than 4900 and Mw/Mn was 2.1.

The resultant polymer was soluble to hexane, benzene, toluene, chloroform and diethyl ether but insoluble in acetone and acetonitrile.

EXAMPLE 2

A 2 ml toluene solution containing 0.898 g (2.04 mmol) of monomer A was cooled to $-42°$ C., to which a 6 ml toluene solution containing 0.449 g (2.04 mmol) of 2,5-di-t-butyl-p-benzoquinone was dropped, stirred at $-42°$ C. for one hour, further stirred at a room temperature for 3 hours, concentrated in vacuum and dried. The yield was quantitative.

$^1$H-NMR (CDCl$_3$): δ0.28(s,SiMe$_3$,36H), 1.26(br,Me$_3$C,18H), 6.56(br,=CH—,2H). $^{13}$C-NMR (CDCl$_3$): δ6.33(SiMe$_3$), 30.93(Me$_3$C), 34.578(Me$_3$C), 121.30(=CH—), 136.10(=C—Bu), 150.05(0—C).

IR (KBr) cm$^{-1}$: 2945,1479,1354,1251,1192,850.

Elementaly analysis: C 46.98 (47.33); H 8.73 (8.56); N 4.11 (4.25).

Values in () indicate the calculated ones those for the alternating copolymer.

The weight average molecular weight measured by GPC was 62,000.

The resultant polymer was soluble in hexane, benzene, toluene, chloroform and diethyl ether but insoluble in acetone and acetonitrile.

EXAMPLE 3

A 5 ml toluene solution containing 1.024 g (2.74 mmol) of the monomer A was cooled to −42° C., to which a 6 ml toluene solution containing 0.630 g (2.74 mmol) of 2,5-di-t-amyl-p-benzoquinone was dropped, stirred at −42° C. for 15 min, further stirred at a room temperature for one hour, concentrated and then dried in vacuum. The yield was quantitative.

$^1$H-NMR (CDCl$_3$): δ0.28(s,SiMe$_3$,36H), 0.70(m,MeCH$_2$, 6H), 1.21(br,Me$_2$C,12H), 1.77(m,MeCH$_2$,4H), 6.44(br,=CH—,2H).

$^{13}$C-NMR (CDCl$_3$): δ6.33(SiMe$_3$), 9.75(MeCH$_2$), 27.97(Me$_2$C), 33.84(MeCH$_2$), 38.11(Me$_2$C), 121.65(=CH—), 135.25(=C-Amyl),150.06(0—C).

IR (KBr) cm$^{-1}$: 2950,1475,1380,1351,1249,1193,1116,855, 751.

The weight average molecular weight measured by GPC was 110,000 and Mw/Mn was 2.8.

The resultant polymer was soluble in hexane, benzene, toluene, chloroform and diethyl ether but insoluble in acetone and acetonitrile.

EXAMPLE 4

A 2 ml toluene solution containing 0.710 g (1.62 mmol) of the monomer A was cooled to −42° C., to which a 2 ml toluene solution containing 0.255 g (1.61 mmol) of 1,4-naphthoquinone was dropped, stirred at −42° C. for 30 min, further stirred at a room temperature for 12 hours, concentrated and then dried in vacuum. The yield was quantitative.

$^1$H-NMR (CDCl$_3$): δ0.30(s,SiMe$_3$,36H), 7.20,8.20(br,Ar,6H).

$^{13}$H-NMR (CDCl$_3$): δ5.48(SiMe$_3$), 111.97(=CH—), 123.24, 124.83, 129.16(Ar), 147.95(0—C).

IR (KBr) cm$^{-1}$: 1582,1374,1264,1224,1071,1008,834,769, 722,663.

The resultant polymer was soluble in hexane, benzene, toluene, chloroform and diethyl ether but insoluble in acetone and acetonitrile.

EXAMPLE 5

A 2 ml toluene solution containing 0.891 g (2.26 mmol) of bis(bis(trimethylsilyl)amide)germanium (II) (hereinafter referred to as monomer B) was cooled to −78° C., to which a 5 ml toluene solution containing 0.250 g (2.31 mmol) of p-benzoquinone was dropped, stirred at −78° C. for 4 hours, further stirred at a room temperature for 20 hours. The resultant product was precipitated in 100 ml of acetone and a supernatant was centrifugally removed and dried in vacuum. The yield was 0.974 g (84% yield).

$^1$H-NMR (CDCl$_3$): δ0.25(s,SiMe$_3$,36H), 6.92(br,Ar,4H).

$^{13}$C-NMR (CDCl$_3$): δ5.54(SiMe$_3$), 120.85(=CH—), 150.12(0—C).

IR (KBr) cm$^{-1}$: 2090,1493,1254,1201,873,841.

The weight average molecular weight of the resultant polymer measured by GPC was 97,000 and Mw/Mn was 2.4.

The resultant polymer was soluble in hexane, benzene, toluene, chloroform and diethyl ether but insoluble in acetone and acetonitrile.

EXAMPLE 6

A 2 ml toluene solution containing 0.907 g (2.31 mmol) of the monomer B was cooled to −78° C., to which a 5 ml toluene solution containing 0.511 g (2.32 mmol) of 2,5-di-t-butyl-p-benzoquinone was dropped, stirred at −78° C. for 4 hours, further stirred at a room temperature for 20 hours. The resultant product was precipitated in 100 ml of acetone and a supernatant was centrifugally removed and dried in vacuum. The yield was 1.007 g (71% yield).

$^1$H-NMR (CDCl$_3$): δ0.29(s,SiMe$_3$,36H), 0.94,1,52(br,Me$_3$C, 18H), 6.78(br,=CH—,2H).

$^{13}$C-NMR (CDCl$_3$): δ6.85(SiMe$_3$),31.56-(Me$_3$C),34.81(Me$_3$C), 121.69(=CH—),136.22(-=C—Bu),150.75(0—C).

IR (KBr) cm$^{-1}$: 2950,1480,1357,1255,1101,1115,849,757,671.

The weight average molecular weight of the resultant polymer measured by GPC was 31,000 and Mw/Mn was 1.6

The resultant polymer was soluble in hexane, benzene, toluene, chloroform and diethyl ether but insoluble in acetone and acetonitrile.

EXAMPLE 7

A 3 ml toluene solution containing 0.605 g (1.54 mmol) of the monomer B was cooled to −78° C., to which a 12 ml toluene solution containing 0.412 g (2.33 mmol) of 2,5-di-t-butyl-p-benzoquinone was dropped, stirred at −78° C. for 5 hours, further stirred at a room temperature for 21 hours. The resultant product was precipitated in 100 ml of acetone and a supernatant was centrifugally removed and dried in vacuum. The yield was 0.578 g (65.8% yield).

$^1$H-NMR (CDCl$_3$): δ0.29(s,SiMe$_3$,36H), 7.59(br,=CH—,2H).

$^{13}$C-NMR (CDCl$_3$): δ5.37(SiMe$_3$), 122.21(=CH—), 145.90(0—C).

IR (KBr) cm$^{-1}$: 1464,1356,1249,1194,1077,849,759.

The weight average molecular weight of the resultant polymer measured by GPC was 65,000 and Mw/Mn was 2.3.

The resultant polymer was soluble in hexane, benzene, toluene, chloroform and diethyl ether but insoluble in acetone and acetonitrile.

EXAMPLE 8

0.63 g (1.60 mmol) of the monomer B and 0.399 g (1.53 mmol) of 2,5-diphenyl-p-benzoquinone were mixed and cooled to −78° C., to which 5 ml of toluene was added, stirred at −78° C. for 2 hours, and further stirred at a room temperature for 20 hours. After removing insoluble parts by the filtration, resultant product was precipitated in 100 ml of acetone and supernatant was centrifugally removed and dried in vacuum. The yield was 0.522 g (53% yield).

$^1$H-NMR (CDCl$_3$): δ0.02(s,SiMe$_3$,36H), 6.97(sh,=CH—,2H), 7.12(br,Ph,10H).

$^{13}$C-NMR (CDCl$_3$): δ5.37(SiMe$_3$), 123.85(=CH—), 127.84, 130.47, 131.50, 138.96(Ar), 146.59(=C—Ph).

IR (KBr) cm$^{-1}$: 1502,1469,1371,1248,1179,849,753.

The weight average molecular weight of the resultant polymer measured by GPC was 64,000 and Mw/Mn was 2.3.

The resultant polymer was soluble to hexane, benzene, toluene, chloroform and diethyl ether but insoluble to acetone and acetonitrile.

EXAMPLE 9

A 3 ml toluene solution containing 0.789 g (2.01 mmol) of the monomer B was cooled to $-78°$ C., to which a 6 ml toluene solution containing 0.254 g (1.61 mmol) of 1,4-naphthoquinone was dropped, stirred at $-78°$ C. for 3 hours, and further stirred at a room temperature for 9 hours. The resultant product was precipitated in 100 ml of acetone and a supernatant was centrifugally removed and dried in vacuum. The yield was 0.815 g (91.8% yield).

$^1$H-NMR (CDCl$_3$): δ0.31(s,SiMe$_3$,36H), 7.06,7.40, 8.10(br, Ar,6H).

$^{13}$C-NMR (CDCl$_3$): δ5.71(SiMe$_3$), 112.59, 123.18, 124.89, 128.71(Ar), 146.19(0—C).

IR (KBr) cm$^{-1}$: 1504,1448,1373,1256,1223,1063,907,869 834.

The weight average molecular weight of the resultant polymer measured by GPC was 360,000 and Mw/Mn was 2.2

The resultant polymer was soluble in hexane, benzene, toluene, chloroform and diethyl ether but insoluble in acetone and acetonitrile.

EXAMPLE 10

Polymerization was conducted in the same procedures as those in Example 5 except for changing the reaction temperature to 0° C.

The yield was 90% and the weight average molecular weight of the resultant polymer as measured by GPC was 80,000, and Mw/Mn was 2.2.

The solubility of the resultant polymer was comparable with that in Example 5.

What is claimed is:

1. A metal-containing polymer represented by the general formula:

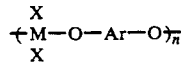

where M represents a group IV metal atom, X represents N(SiR$^1$R$^2$R$^3$)$_2$ or N(R$^4$)SiR$^1$R$^2$R$^3$, each of R$^1$, R$^2$, R$^3$ and R$^4$ represents an alkyl group or aryl group, Ar represents a (substituted) phenylene, (substituted) naphthylene or (substituted) anthrylene group, and n represents an integer of 2 to 5000.

2. A metal-containing polymer as defined in claim 1, wherein the group IV metal atom is selected from silicon, germanium, tin and lead.

3. A metal-containing polymer as defined in claim 1, wherein each of R$^1$, R$^2$, R$^3$ and R$^4$ represents a C$_1$-C$_{20}$ alkyl or aryl group.

4. A metal-containing polymer as defined in claim 1, wherein a substituent for the (substituted) phenylene, (substituted) naphthylene or (substituted) anthrylene is an alkyl, aryl, halogen or nitrile.

5. A process for producing metal-containing polymer represented by the general formula:

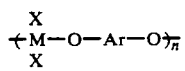

where M represents a group IV metal atom, X represents N(SiR$^1$R$^2$R$^3$)$_2$ or N(R$^4$)SiR$^1$R$^2$R$^3$, each of R$^1$, R$^2$, R$^3$ and R$^4$ represents an alkyl group or aryl group, Ar represents a (substituted) phenylene, (substituted) naphthylene or (substituted) anthrylene group, and n represents an integer of 2 to 5000, wherein alternating copolymerization is conducted by using a compound represented by the general formula:

where M represents a group IV metal atom, X represents N(SiR$^1$R$^2$R$^3$)$_2$ or N(R$^4$)SiR$^1$R$^2$R$^3$, each of R$^1$, R$^2$, R$^3$ and R$^4$ represents an alkyl group or aryl group, as a reductant monomer, and a (substituted) benzoquinone, (substituted) naphthoquinone or (substituted) anthraquinone as the oxidant monomer.

6. A process as defined in claim 5, wherein the reaction between the reductant monomer and the oxidant monomer is conducted under the presence of a solvent selected from aromatic solvent and ether solvent.

7. A process as defined in claim 5, wherein the reaction between the reductant monomer and the oxidant monomer is conducted at a temperature from $-100°$ C. to 100° C.

8. A process as defined in claim 5, wherein the reaction between the reductant monomer and the oxidant monomer is conducted at a temperature from $-78°$ C. to 50° C.

* * * * *